United States Patent [19]

Gutman

[11] 4,096,272
[45] Jun. 20, 1978

[54] PHENOXYOXADIAZOLE CYCLOPROPANE CARBOXYLATES AS INSECTICIDES

[75] Inventor: Arnold D. Gutman, Berkeley, Calif.

[73] Assignee: Stauffer Chemical Company, Westport, Conn.

[21] Appl. No.: 796,775

[22] Filed: May 13, 1977

[51] Int. Cl.² .................... C07D 271/06; A01N 9/22
[52] U.S. Cl. ............... 424/272; 260/307 G; 260/564 G
[58] Field of Search .................. 260/307 G; 424/272

[56] References Cited

U.S. PATENT DOCUMENTS 3,879,407   4/1975   Hagarty .................. 260/302 D

*Primary Examiner*—Raymond V. Rush
*Attorney, Agent, or Firm*—Edwin H. Baker

[57] ABSTRACT

Compounds of the formula

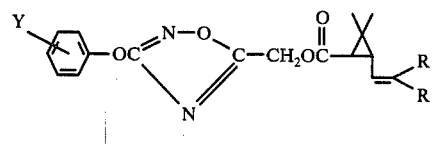

in which R is methyl, chlorine or bromine and Y is hydrogen or methyl, useful as insecticides.

15 Claims, No Drawings

PHENOXYOXADIAZOLE CYCLOPROPANE CARBOXYLATES AS INSECTICIDES

This invention relates to certain novel chemical compounds and their use as insecticides. More particularly, this invention relates to certain novel phenoxyoxadiazole cyclopropane carboxylates which are useful as insecticides.

The compounds of the present invention that are useful as insecticides are those having the structural formula

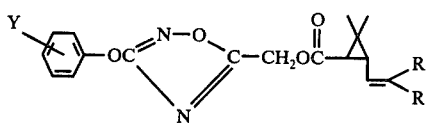

in which R is methyl, chlorine or bromine, preferably methyl and chlorine, and Y is hydrogen or methyl. Preferably Y is hydrogen.

The compounds of this invention can be prepared according to the following reaction steps:

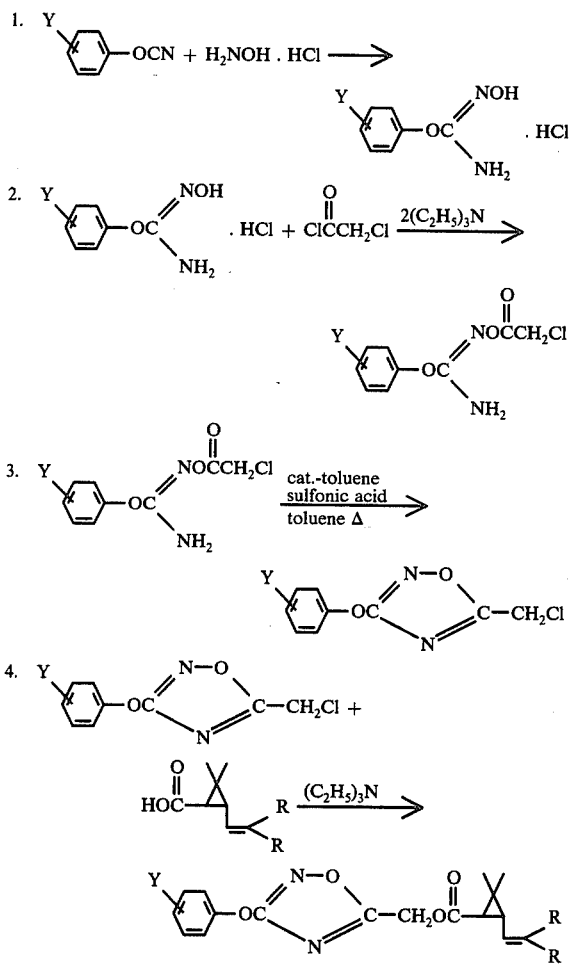

Preferably, reaction step 1 is carred out by slowly adding an equimole amount of the cyanate reactant to a solution of the hydroxylamine hydrochloride reactant while maintaining the reaction temperature at about 30°–35° C. The reaction is continued at room temperature until completed. The product is recovered and purified by conventional techniques.

Preferably, reaction step 2 is carried out by slowly adding an equimole amount of the chloroacetyl chloride reactant a solution of the phenoxy formamide hydrochloride reactant with stirring and cooling to around 0° C. About one mole of a hydrochloric acid acceptor, such as triethylamine, is added at the same temperature before and after the addition of the chloroacetyl chloride. The reaction is then continued for about one hour with stirring at the same temperature. After the reaction is complete, the salt is removed by filtration. Next, the solvent is removed and the reaction product is recovered and purified by conventional techniques.

Preferably, reaction step 3 is run by forming a solution of the reaction product of step 2. The solvent being one not miscible with water, such as toluene. The solution is heated at reflux in the presence of an acid catalyst such as toluene sulfonic acid, napthalene sulfonic acid or sulfuric acid until all water of reaction is removed. The intermediate reaction product of step 3 is recovered and purified by standard procedures.

Preferably, reaction step 4 is carried out by refluxing a mixture of the reaction product of step 3 with an excess of the carboxylic acid reactant and an equimole amount of a hydrochloride acid acceptor such as triethylamine. After heating at reflux for about two hours, the reaction mixture is cooled and the desired reaction product is recovered and purified by conventional techniques.

The synthesis of the compounds of this invention is specifically illustrated in the following examples.

EXAMPLE I

PHENOXY FORMAMIDE OXIME HYDROCHLORIDE

This example teaches the synthesis of a representative intermediate of reaction step 1.

First, 6.95 grams (0.1 mole) of hydroxylamine hydrochloride and 50 milliliters of methanol were combined and stirred in a 100 milliliter 2-neck flask fitted with a thermometer and dropping funnel. Next, 11.9 grams (0.1 mole) of phenyl cyanate were slowly added through the dropping funnel at such a rate that the reaction temperature was maintained at 30° to 35° C. After the addition was completed, the reaction mixture was stirred at room temperature for 30 minutes. The methanol was then removed in vacuo at 45° C and the residue was triturated with 200 milliliters of ethyl ether. A solid white product was collected by filtration and oven dried at 50° to yield 14.8 grams (78.5% of theory) of the desired intermediate, phenoxy formamide oxime hydrochloride.

EXAMPLE II

O-CHLOROACETYLPHENOXY FORMAMIDE OXIME

This example teaches the synethesis of a representative intermediate of reaction step 2 using the intermediate prepared in Example I.

First, 9.4 grams (0.05 mole) of the reaction product of Example I was combined with 100 milliliters of dry acetone in a 200 milliliter round bottom flask fitted with a dropping funnel and thermometer. A suspension formed and it was cooled to 0° C. with stirring. Next, 7.5 milliliters of triethylamine was added to the suspension at such a rate that the temperature was maintained at 0° C. Next, 5.6 grams (0.05 mole) of chloroacetylchloride was added at 0° C. followed by the addition of 7.5 milliliters of triethylamine added at 0° C. After the additions were completed, the mixture was stirred at 0° C. for one hour and then was filtered free of salt. The filtrate was evaporated in vacuo at 50° C. The residue was taken up in 200 milliliters of benzene followed by washing with 100 milliliters of ice water. The benzene phase was then dried with MgSO$_4$ and evaporated in vacuo at 50° C. to yield 7.4 grams (64.7% of theory) of the desired product, O-chloroacetylphenoxy formamide oxime, which had a melting point of 79°–83° C.

EXAMPLE III
3-PHENOXY-5-CHLOROMETHYL-1,2-4-OXADIAZOLE

This example teaches the synthesis of a representative intermediate of reaction step 3 using the intermediate prepared in Example II.

First, 2 grams (.0087 mole) of the reaction product of Example II was combined with 150 milliliters of toluene and 0.1 gram of toluene sulfonic acid in a 250 milliliter round bottom flask, fitted with a Dean Stark trap and condenser. The solution was heated under reflux until water evolution ceased. The toluene was then removed in vacuo at 50° C. to yield 1.6 grams (87.3% of theory) of the desired product, 3-phenoxy-5-chloromethyl-1,2,4-oxadiazole having a refractive index of $n_D^{30}$ 1.5168.

EXAMPLE IV
3-PHENOXY-5-[3-(2,2-DICHLOROVINYL)2,2-DIMETHYLCYCLOPROPANECARBOXYMETHYL]1,2,4-OXADIAZOLE

This example teaches the synthesis of a compound of this invention according to reaction step 4 using the intermediate of Example III.

First, 1.4 grams (0.0066 mole) of the reaction product of Example III, 3.0 grams (0.008 mole) of 2,2-dimethyl-3-(2,2-dichlorovinyl) cyclopropane carboxylic acid, 0.8 grams (0.008 mole) of triethylamine and 50 milliliters of methylethylketone were combined in a flask and heated under reflux for two hours. After cooling to room temperature, the mixture was poured into 250 milliliters of benzene. The benzene solution was then washed twice with 150 milliliter portions of water. The benzene phase was dried with MgSO$_4$ and evaporated to yield 2.3 grams (90.9% of theory) of the desired compound, 3-phenoxy-5-[3-(2,2-dichlorovinyl)2,2-dimethylcyclopropanecarboxymethyl]1,2,4-oxadiazole, having a refractive index of $n_D^{30}$ 1.5050.

The following is a table of certain selected compounds that are preparable according to the procedure described hereto. Compound numbers are assigned to each compound and are used throughout the remainder of the specification.

TABLE I

| Compound Number | R | Y | $n_D^+$ |
|---|---|---|---|
| 1[a] | Cl | H | 1.5050 |
| 2 | CH$_3$ | H | 1.4961 |
| 3 | CH$_3$ | 3-CH$_3$ | 1.4942 |

TABLE I-continued

| Compound Number | R | Y | $n_D^+$ |
|---|---|---|---|
| 4 | Cl | 3-CH$_3$ | 1.5060 |

[a]Prepared in Example IV

INSECTICIDAL EVALUATION TESTS

The compounds of Table I were found to have insecticidal activity against the following insect species which were used in the evaluation tests described hereafter.

1. Housefly (HF) - *Musca domestica* (Linn.)
2. Black Bean Aphid (BBA) - *Aphis fabae* (Scop.)
3. Green Peach Aphid (GPA) - *Myzus persicae* (Sulzer)
4. Saltmarsh Caterpillar (SMC) - *Estigeme acrea* (Drury)
5. Cabbage Looper (CL) - *Trichoplusia ni* (Hubner)
6. Tobacco Budworm (TBW) - *Heliothis virescens* (F.)
7. Southern House Mosquito (MOS) - *Culex pipiens quinquefasciatus* (Say)

The insecticidal evaluation tests were conducted as follows:

Housefly: Test compounds were diluted in acetone and aliquots pipetted onto the bottom of 55 × 15 millimeter aluminum dishes. To insure even spreading of the chemical on the bottom of the dishes, one milliliter of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD$_{50}$ values are expressed below in Table II under the heading "HF", in terms of μg of the test compound per 25 female flies.

Black Bean Aphid: Nasturtium plants (*Tropaeolum sp.*), approximately five centimeters tall, were transplanted into sandy loam soil in 3-inch clay pots and infested with 25–50 black bean aphids of mixed ages. Twenty-four hours later they were sprayed to the point of runoff with 50-50 acetone-water solutions of the test chemicals. Treated plants were held in the greenhouse and mortality was recorded after 48 hours. Test concentrations ranged from 0.05% down to that at which 50% mortality occurred. LD$_{50}$ values are expressed below in Table II under the heading "BBA" in terms of percent of the test compound in the sprayed solution.

Green Peach Aphid: Radish plants (Rhaphanus sativus), approximately two centimeters tall, were transplanted into sandy loam soil in three-inch clay pots and infested with 25–50 green peach aphids of mixed ages. Twenty-four hours later they were sprayed to the point of runoff with 50-50 acetone-water solutions of the test chemicals. Treated plants were held in the greenhouse and mortality was recorded after 48 hours. Test concentrations ranged from 0.05% down to that at which 50% mortality occurred. LD$_{50}$ values are expressed below in Table II under the heading "GPA" in terms of percent of the test compound in the sprayed solution.

Saltmarsh Caterpillar: Test compounds were diluted in a 50-50 acetone-water solution. Sections of curly dock (*Rumex crispus*) leaves, approximately 1 × 1.5 inches, were immersed in the test solution for two-three seconds and placed on a wire screen to dry. The dried leaves were placed in petri dishes containing a moistened piece of filter paper and infested with five second-instar saltmarsh caterpillar larvae. Mortality of the larvae was recorded 48 hours later, and a piece of synthetic media was added to dishes containing survivors. These were then held for five additional days to observe for any delayed effects of the test chemicals. Test concentrations ranged from 0.05% down to that at which approximately 50% mortality occurred. $LD_{50}$ values are expressed below in Table II under the heading "SMC" in terms of percent of the test compound in the solution.

Cabbage Looper: Test compounds were diluted in a 50-50 acetone-water solution. Cotyledons of hyzini squash (*Calabacita abobrinha*), approximately 1 × 1.5 inches, were immersed in the test solutions for two-three seconds and placed on a wire screen to dry. The dried leaves were placed in petri dishes containing a moistured piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals. Test concentrations ranged from 0.1% to that at which approximately 50% mortality occurred. $LD_{50}$ values are expressed below in Table II under the heading "CL" in terms of percent of the test compound in the solution.

Tobacco Budworm: Test compounds were diluted in a 50-50 acetone-water solution. Sections of Romaine lettuce (*Latuca sativa*) leaves, approximately 1 × 1.5 inches, were immersed in the test solutions for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for 5 additional days to observe for any delayed effects of the test chemicals. Test concentrations ranged from 0.1% to that at which approximately 50% mortality occurred. $LD_{50}$ values are expressed below in Table II under the heading "TBW" in terms of percent of the test compound in the solution.

Southern House Mosquito Larvae (*Culex pipiens quinquefasciatus* Say): Insecticidal activity was determined using third instar larvae of the mosquito *Culex pipiens quinquefasciatus*. Ten larvae were placed in a six ounce paper cup containing 100 milliliters of an aqueous solution of the test chemical. The treated larvae were stored at 70° F. and 48 hours later the mortality was recorded. Test concentrations ranged from one ppm down to that at which approximately 50% mortality occurred. $LD_{50}$ values are expressed below in Table II under the heading "MOS" in terms of ppm of the test compound in the solution.

TABLE II

| Compound Number | HF (μg) | BBA (%) | GPA (%) | SMC (%) | CL (%) | TBW (%) | MOS (ppm) |
|---|---|---|---|---|---|---|---|
| 1 | 8.8 | .002 | .005 | .03 | .02 | .03 | .008 |
| 2 | 40 | — | — | — | .10 | — | .2 |
| 3 | 100 | — | — | .05 | .10 | — | 1.0 |
| 4 | 28 | .008 | .03 | .05 | .08 | .10 | .1 |

TABLE II-continued

The compounds of this invention are generally formulated into a form suitable for convenient application. For example, the compounds can be prepared into a pesticidal composition in the form of emulsions, suspensions, solutions, dusts or aerosol sprays. In general, such pesticidal compositions will contain, in addition to the active compound, the inert adjuvants which are found normally in pesticide preparations. In these compositions, an active compound of this invention can be employed as the sole pesticide component or it can be used in an admixture with other compounds having similar utility.

The pesticide compositions of this invention can contain, (a) liquid adjuvants, such as organic solvents, sesame oil, xylene range solvents, heavy petroleum, etc.; water; (b) emulsifying agents; (c) surface active agents; (d) solid adjuvants such as talc; pyrophyllite, diatomite; gypsum; clays or (e) propellants, such as dichlorodifluoromethane, etc.

If desired, however, the active compounds can be applied directly to feedstuffs, seeds, etc., or upon other materials upon which the pests feed. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active compound in the aforesaid compositions can vary within wide limits, ordinarily the active compound will comprise between about 1 and about 95% by weight of the pesticidal composition and more preferably between about 5 to 80% by weight.

I claim:

1. A compound of the formula

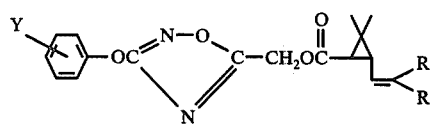

in which each R is methyl or each R is chlorine and Y is hydrogen or 3-methyl.

2. The compound of claim 1 in which R is chlorine and Y is hydrogen.

3. The compound of claim 1 in which R is methyl and Y is hydrogen.

4. The compound of claim 1 in which R is methyl and Y is 3-methyl.

5. The compound of claim 1 in which R is chlorine and Y is 3-methyl.

6. A pesticidal composition comprising a compound of the formula

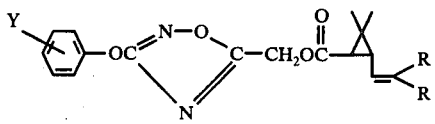

in which each R is methyl or each R is chlorine and Y is hydrogen or 3-methyl and an inert adjuvant.

7. The pesticidal composition of claim 6 in which R is chlorine and Y is hydrogen.

8. The pesticidal composition of claim 6 in which R is methyl and Y is hydrogen.

9. The pesticidal composition of claim 6 in which R is methyl and Y is 3-methyl.

10. The pesticidal composition of claim 6 in which R is chlorine and Y is 3-methyl.

11. A method of controlling insects comprising applying to the habitat thereof an insecticidally effective amount of a compound of the formula

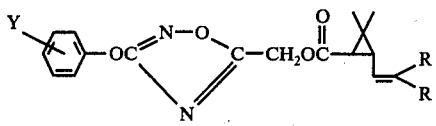

in which each R is methyl or each R is chlorine and Y is hydrogen or 3-methyl.

12. The method of claim 11 in which R is chlorine and Y is hydrogen.

13. The method of claim 11 in which R is methyl and Y is hydrogen.

14. The method of claim 11 in which R is methyl and Y is 3-methyl.

15. The method of claim 11 in which R is chlorine and Y is 3-methyl.

* * * * *